United States Patent [19]
Phillips

[11] 3,946,071

[45] Mar. 23, 1976

[54] SUBSTITUTED ALPHA-CHLORO-METHANE-SULFENYL CHLORIDES

[75] Inventor: Wendell Gary Phillips, Olivette, Mo.

[73] Assignee: Monsanto Company, St. Louis, Mo.

[22] Filed: Dec. 7, 1973

[21] Appl. No.: 422,638

Related U.S. Application Data

[62] Division of Ser. No. 139,977, May 3, 1971, Pat. No. 3,803,224.

[52] U.S. Cl..... 260/543 H; 260/239 B; 260/293.85; 260/326.5 S
[51] Int. Cl.² ........................................ C07C 145/00
[58] Field of Search...... 260/326.5 S, 293.85, 239 B

[56] References Cited
UNITED STATES PATENTS 3,547,994   12/1970   Ratts .............................. 260/481 R

OTHER PUBLICATIONS

Kuehle: *Synthesis*, 1970, (11), pp. 561–580.

*Primary Examiner*—James A. Patten
*Assistant Examiner*—Killos
*Attorney, Agent, or Firm*—William I. Andress

[57] ABSTRACT

Substituted alpha-chloro-methane-sulfenyl chlorides, intermediary chlorinated benzyl sulfides and chlorinated mercaptans useful as herbicides and chemical intermediates for herbicides are prepared by the chlorination of substituted methyl benzyl sulfides and substituted methyl mercaptans.

3 Claims, No Drawings

SUBSTITUTED ALPHA-CHLORO-METHANE-SULFENYL CHLORIDES

This is a division of application Ser. No. 139,977, filed May 3, 1971, now U.S. Pat. No. 3,803,224.

This invention relates to substituted alpha-chloromethane-sulfenyl chlorides of the formulas

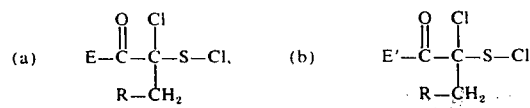

and

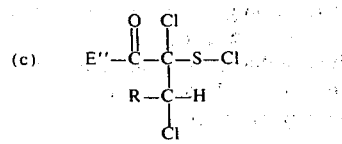

as well as intermediary compounds of the formulas

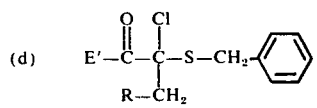

and

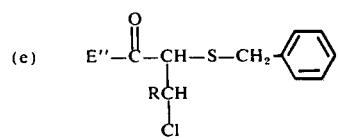

and their manufacture by reaction of chlorine, sulfuryl chloride or mixtures thereof with the corresponding precursors of the formulas

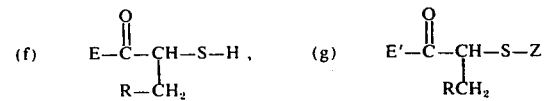

and

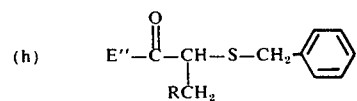

wherein R is hydrogen or alkyl of from 1 to 3 carbons, E is amino, E' is alkoxy, E'' is aryl or halogenated aryl, and Z is hydrogen or benzyl.

Preferred amino are represented by the formula

wherein Q and Q' are each hydrogen, alkyl of from 1 through 5 carbons, alkoxyalkyl, aryl and halogenated aryl.

Preferred alkoxy are lower alkoxy of from 1 through 5 carbon atoms. More preferred are methoxy, ethoxy, propoxy, isopropoxy, butoxy and secbutoxy. Still more preferred are methoxy and ethoxy.

Preferred aryls include phenyl, tolyl, dimethylphenyl, ethylphenyl, diethylphenyl, trimethylphenyl, triethylphenyl, propylphenyl, cumenyl, and trihalomethylphenyl. More preferred are phenyl and tolyl. Still more preferred is phenyl.

Preferred halogenated aryls include halophenyl, dihalophenyl and trihalophenyl. More preferred are bromophenyl, fluorophenyl, chlorophenyl, dibromophenyl, difluorophenyl, dichlorophenyl and trichlorophenyl. Still more preferred are chlorophenyl, dichlorophenyl and trichlorophenyl.

Examples of amino present in the compounds of the present invention used in or made by the method of the present invention include, but are not limited to, amino, methylamino, ethylamino, propylamino, isopropylamino, butylamino, secbutylamino, methoxymethylamino, ethoxymethylamino, propoxymethylamino, butoxymethylamino, dimethylamino, diethylamino, di-isopropylamino, phenyl methoxymethylamino, phenyl ethoxymethylamino, phenyl propoxymethylamino, tolyl methoxymethylamino, halophenyl ethoxymethylamino and alkyleneamino wherein alkylene forms a continuous chain between the terminal valence bonds of the nitrogen atom of from 4 through 8 carbon atoms, as well as anilino, paraalkylanilino, ortho-alkylanilino, 2,6-dialkylanilino, 2,4,6-trialkylanilino and 3,4,5-trialkylanilino wherein alkyl is methyl, ethyl, isopropyl and tertbutyl and meta-trihalomethylanilino, para-haloanilino, ortho-haloanilino, 2,6-dihaloanilino, 2,4,6-trihaloanilino, and 3,4,5-trihaloanilino wherein halo is chloro, bromo or fluoro.

In the overall manufacture of substituted alpha-chloro-methane-sulfenyl chlorides of this invention from the corresponding precursors, a reaction occurs which, while not completely understood in the manner of its mechanism, can be represented by the following chemical equations, wherein E, E', E'', R and Z have the aforementioned significance:

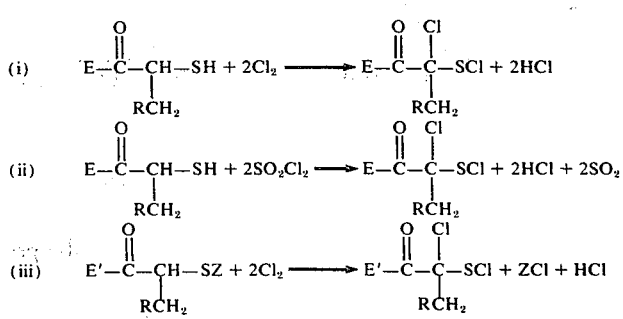

(iv) 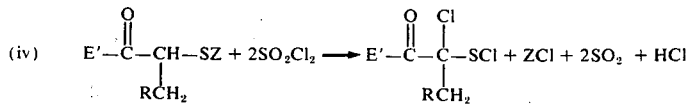

(v) 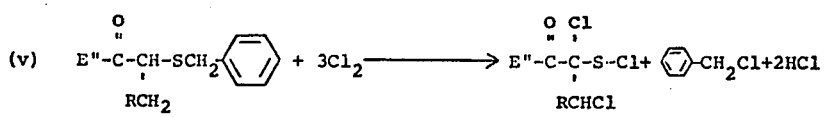

(vi) 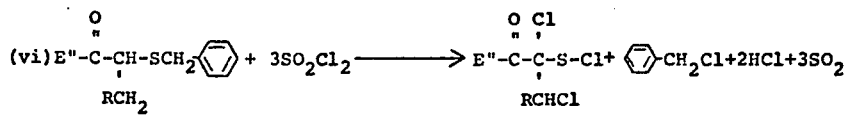

By controlling the quantity of chlorinating agent, i.e. chlorine, sulfuryl chloride, or mixtures thereof the above reactions appear to proceed in a stepwise fashion as illustrated by the following chemical equations.

From the foregoing equations (vii), (viii), (ix), and (x), it is clear that the reactions described by said equations may be conducted in one or two steps by control of the concentration of the chlorinating agents. Thus, if the intermediary product (vii) 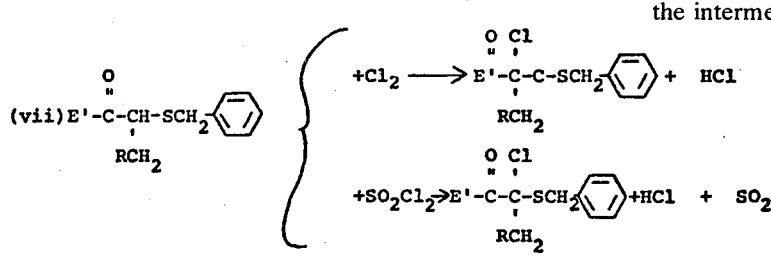

(viii) 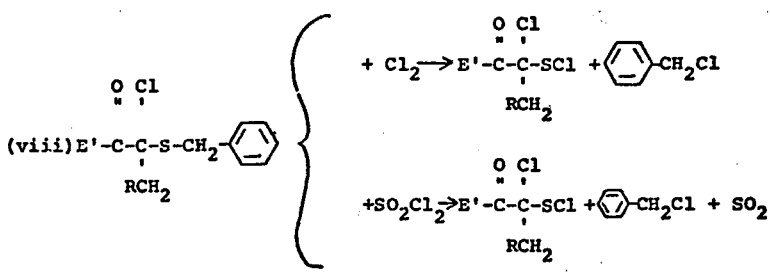

(ix) 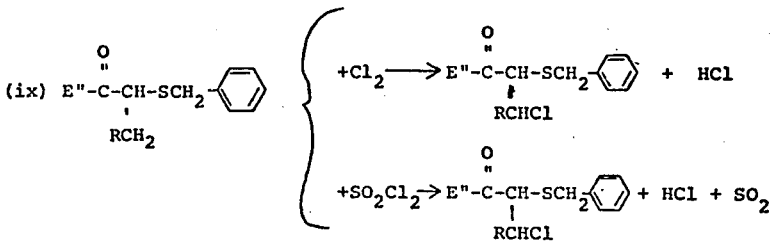

(x) 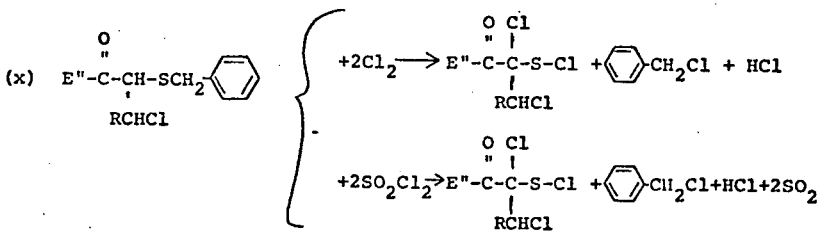

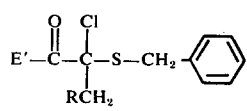

[the product of equation (vii)] or

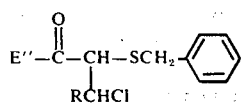

[the product of equation (ix)] is the desired product, it is obtained by mixing in an inert organic liquid to effect evolution of hydrogen chloride, one molecular proportion of precursor substituted methyl-benzyl sulfide and about one molecular proportion of chlorine or sulfuryl chloride (when sulfuryl chloride is employed instead of chlorine in whole or in part sulfur dioxide also evolves as a by-product along with by-product hydrogen chloride) at a temperature above the freezing point of the system. The said intermediary product is readily isolated from this reaction mass, as for example by evaporation of the inert organic liquid and recrystallization of the residue in the cold to give the intermediate product. The yield of the said intermediary is generally 100 percent, but declines as the reaction temperature increases above the range of from about 25°C to about 30°C, the formation of benzyl chloride being observed. Since the chlorination appears to proceed in a stepwise fashion, the intermediary product may likewise be obtained even when the chlorinating agent is present in quantities greater than the stoichiometric amount so long as reaction conditions are very mild, i.e., the temperature is maintained below 20 degrees Centigrade and reaction time does not exceed about one hour.

In the overall process of this invention for the preparation of substituted alpha-chloro-methane-sulfenyl chlorides, as represented by equations (i) through (vi), the chlorinating agent may be chlorine alone, sulfuryl chloride alone, or a mixture of any proportion of chlorine and sulfuryl chloride. The chlorinating agent may be present in excess and the reaction may be carried out at any temperature from above the freezing point of the system to about the boiling point of the system at the desired pressure under which the reaction is conducted.

Since gaseous reaction products are evolved the reaction is usually carried out at atmospheric pressure but higher or lower pressures may be utilized if equipment and other factors favor such higher or lower pressures. The reaction may be carried out in an open vessel or under reflux.

It is preferable to conduct the reaction in the presence of an inert organic liquid but when reaction conditions are mild, i.e. the reaction is conducted at a temperature below about 70°C., an excess of sulfuryl chloride may perform the solvating function of the inert organic liquid and there is no necessity for the inert liquid in the reaction system. In a preferred embodiment of the process for the preparation of substituted alpha-chloro-methane-sulfenyl chloride in the presence of an inert organic liquid there will be employed for each mole of precursor substituted methylbenzyl sulfide or substituted methyl mercaptan from 2 to 6 moles of chlorine or sulfuryl chloride or mixture thereof. The reaction is preferably carried out at a temperature above the freezing point of the system but below the boiling point of the inert organic liquid. More preferably the reaction is carried out at temperatures of from about 0 degrees centigrade to about 100°C, and still more preferably from about 0° to about 70°C.

Precursor amido-substituted methyl mercaptans are readily obtainable by initially slowly mixing at about room temperature one molecular proportion of an appropriate amine, substituted amine, aniline or substituted aniline, E-H, with an acid,

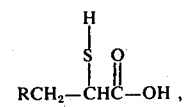

selected to give the desired substituted methyl mercaptan,

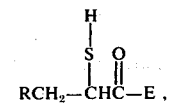

thereafter refluxing for from about 3 to about 6 hours, cooling the mass to about room temperature, separating the mercaptan from the cooled mass by conventional means, washing the mercaptan with a dilute aqueous acid solution and, if necessary, recrystallizing or distilling the product to purify same.

Precursor carbalkoxy-substituted methyl mercaptans are readily obtainable by initially slowly mixing at about room temperature one molecular proportion of an appropriate alcohol, E'-H, with an acid,

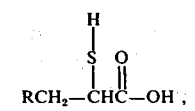

selected to give the desired substituted methyl mercaptan,

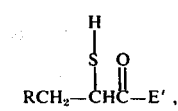

thereafter refluxing in the presence of an excess of the alcohol in an acidic medium for from about 1 to 3 hours, cooling the mass to about room temperature, stripping off the excess alcohol, and, if necessary, recrystallizing or distilling the product to purify same.

Precursor substituted methyl benzyl sulfides are readily obtainable by initially slowly mixing at about room temperature one molecular proportion of a substituted alpha-halo-alkyl-carbonyl,

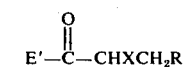

or

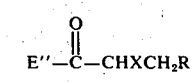

wherein X is halo, corresponding to the desired substituted methylbenzyl sulfide with an aqueous solution containing one molecular proportion of benzyl mercaptan and one molecular proportion of sodium hydroxide, thereafter refluxing the so-charged mass for about twelve hours, cooling to about room temperature, extracting the cooled mass with methylene chloride, and then separating the product by evaporating methylene chloride from the extract, and if necessary, vacuum distilling the product to purify same.

The inert organic liquid employed in the overall manufacture of this invention or any portion thereof can be any organic liquid, or mixtures thereof, which is inert under the reaction conditions, and preferably that having a boiling point in the range of from about 30°C. to about 100°C. Ordinarily, the inert organic liquid comprises liquid alkanes or liquid chloroalkanes or various mixtures thereof, for example; pentane, 3-ethylpentane, hexane, 2-ethylhexane, heptane, dichloromethane, 1,1-dichloroethane, chloroform, carbon tetrachloride, isobutyl chloride, and various mixtures thereof. In general it is preferable, but not necessary, that the amount of said inert organic liquid present throughout the course of the reaction be that at least sufficient to maintain the intermediary alpha-chloromethylbenzyl sulfide in solution. Where the reactions are carried out in step-wise fashion in proceeding from intermediary alpha-chloromethylbenzyl sulfides to an alpha-chloro-alpha-(chloromercapto)-compound the inert organic liquid will usually be the same as that employed in preparing the intermediary or intermediaries; however, such can be replenished or replaced in whole or in part by a different inert organic liquid in any or each step.

In the matter of pressure, either that above or below atmospheric pressure can be employed, however, in general atmospheric pressure will be satisfactory.

Substituted alpha-chloro-methane-sulfenyl chlorides exhibit herbicidal activity toward noxious weeds and have particular utility as selective pre-emergent herbicides.

As illustrative of this invention but not limitative thereof is the following:

EXAMPLES 1 THROUGH 4

These examples illustrate the preparation of substituted methyl mercaptans having the formulas

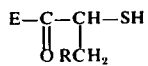

and

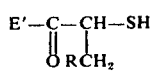

which mercaptans are precursors to the compounds of the present invention.

EXAMPLE 1

To a suitable reaction vessel equipped with a thermometer, agitator and venting means are charged approximately 65 parts by weight of ortho-chloroaniline (about ½ mole) and approximately 53 parts by weight of thiolactic acid (about ½ mole). The contents of the so-charged vessel are heated with agitation under a nitrogen atmosphere to about 130°C. and maintained at that temperature for about 4 hours. The contents are cooled to about room temperature and washed with a dilute HCl solution. A white solid is isolated by filtration, dissolved in and recrystallized from chloroform, and identified as alpha-mercapto-ortho-chloropropanilide (melting point of 83° to 90°C.

Alpha-mercapto-alpha-methyl-ortho-chloropropanilide exhibits pre-emergent herbicidal activity against morning glory and Johnson grass.

EXAMPLE 2

The procedure of Example 1 is followed except that in place of 65 parts by weight of ortho-chloroaniline an equimolecular proportion of aniline is charged to the vessel. Alpha-mercaptopropanilide is obtained.

In similar fashion other ring substituted alpha-mercaptopropanilides may be prepared from the appropriate substituted aniline. Likewise, by charging to the reactor in place of the thiolactic acid and equal molecular proportion of higher acids in the thiolactic acid series substituted alpha-acetanilido substituted methyl mercaptans having the formula

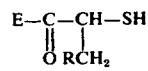

wherein R is methyl, ethyl, propyl and isopropyl may be prepared.

EXAMPLE 3

The procedure of Example 1 is followed except that in place of 65 parts by weight of ortho-chloroaniline an equimolecular proportion of diethyl amine is charged to the vessel. N,N-diethyl-alpha-mercapto-propionamide is obtained.

In similar fashion other N-substituted alpha-mercapto-propionamides may be prepared from the appropriate N-substituted amide. Likewise, by charging to the reactor in place of the thiolactic acid an equal molecular proportion of higher acids in the thiolactic acid series substituted alpha-amido-substituted methylmercaptans having the formula

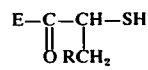

wherein R is methyl, ethyl, propyl and isopropyl may be prepared.

EXAMPLE 4

To a suitable reaction vessel equipped with a thermometer, agitator and venting means are charged approximately 500 parts by weight of isopropyl alcohol and approximately 53 parts by weight of thiolactic acid (about ½ mole). To the so-charged mass is added about 1 part by weight of concentrated $H_2SO_4$. The contents of the so-charged vessel are heated with agitation under a nitrogen atmosphere to reflux temperature and maintained at that temperature for about 4 hours. The contents are cooled to about room temperature. Excess alcohol is stripped off by distillation under vacuum. The liquid product may be vacuum distilled if a high purity product is desired. Isopropyl-alpha-mercaptopropionate is obtained.

In similar fashion, other substituted alpha-mercapto esters may be prepared from the appropriate alcohols. Likewise, by charging to the reactor in place of the thiolactic acid an equal molecular proportion of higher acids in the thiolactic acid series, alpha-mercapto esters having the formula

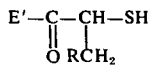

wherein R is methyl, ethyl, propyl and isopropyl may be prepared.

EXAMPLES 5 AND 6

These examples illustrate the preparation of substituted methyl benzyl sulfides having the formulas

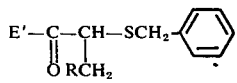

and

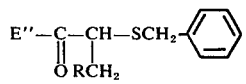

which sulfides are precursors to the compounds of the present invention.

EXAMPLE 5

To a suitable reaction vessel equipped with a thermometer and agitator with an aqueous solution containing approximately 200 parts by weight of water and approximately 20 parts by weight of sodium hydroxide is added with agitation approximately 62 parts by weight of benzyl mercaptan. Thereafter approximately 91 parts by weight of ethyl alpha-bromopropionate is added with agitation. Thereupon the mass is agitated at room temperature for about 1 hour. Thereafter the water is distilled off leaving a liquid identified as ethyl alpha-(benzylmercapto)-propionate. Similarly other alpha-(benzylmercapto)-esters may be prepared from the corresponding alpha-halo-ester.

EXAMPLE 6

To a suitable reaction vessel equipped with a thermometer and agitator charged with an aqueous solution containing approximately 200 parts by weight of water and approximately 16 parts by weight of sodium hydroxide is added with agitation approximately 49.6 parts by weight of benzyl mercaptan. Thereafter a hot ethanol solution containing approximately 785 parts by weight of ethanol and approximately 85.2 parts by weight of alpha-bromo-propiophenone is added with agitation. The reation is exothermic and temperature is permitted to rise. As the temperature begins to subside approximately 1000 parts by weight of water is added with agitation. Thereafter the mass is extracted with methylene chloride, the extracts combined and subjected to evaporation of methylene chloride. The residue, a solid, is alpha-(benzylmercapto)-propiophenone.

In a similar manner the following precursors of the manufacture of this invention are prepared: alpha-(benzylmercapto)-3,4,5-trichloropropiophenone, alpha-(benzylmercapto)-2,4-dibromopropiophenone, alpha-(benzylmercapto)-ortho-bromopropiophenone, alpha-(benzylmercapto)-meta-chloropropiophenone, alpha-(benzylmercapto)-para-chloropropiophenone, alpha-(benzylmercapto)-parabromopropiophenone, alpha-(benzylmercapto)-para-fluoropropiophenone, employing benzyl mercaptan and the appropriate substituted acetophenone, for example, alpha-chloro-3,4,5-trichloropropiophenone, alpha-bromo-2,4-dibromopropiophenone, alpha-bromo-ortho-bromopropiophenone, alpha-chloro-ortho-fluoropropiophenone, alpha-chloro-meta-chloropropiophenone, alpha-chloro-para-chloropropiophenone, alpha-bromo-para-bromopropiophenone, alpha-chloropara-fluoropropiophenone and the like, in the presence of a hydrogen halide scavenging agent. Likewise trihalomethyl, alkyl, dialkyl and trialkyl substituted phenones and higher aromatic ketones can be prepared by the above-described methods and used in the manufacture of alpha-chloro-alpha-aroyl-methane-sulfenyl chlorides and intermediary products by the method of the present invention.

EXAMPLES 7 THROUGH 14

These examples illustrate the preparation of substituted alpha-chloro-methane-sulfenyl chlorides of the formula

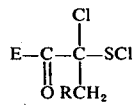

and

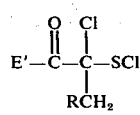

by the process of the present invention.

EXAMPLE 7

This example is illustrative of the preparation of ethyl alpha-(chloromercapto)-alpha-chloropropionate from ethyl-alpha-(benzylmercapto)-propionate and sulfuryl chloride.

To a suitable reaction vessel equipped with a thermometer, agitator and venting means is charged approximately 22.4 parts by weight of ethyl alpha-(benzylmercapto)-propionate dissolved in approximately 275 parts by weight of methylene chloride. While agitating the so-charged mass at about 0°C is slowly added approximately 50 parts by weight of sulfuryl chloride. The reaction is exothermic and the temperature during the addition is permitted to rise to about 20°C. Upon completion of the sulfuryl chloride addition the mass is agitated for about one hour at about room temperature. Thereafter the mass is stripped of volatiles under vacuum to give a liquid residue [composed chiefly of an equimolar mixture of ethyl alpha-(chloromercapto-alpha-chloropropionate and by-product benzyl chloride] which residue is fractionally distilled and the yellow liquid collected at 85°–86°C at 13 mm. of mercury is identified as ethyl alpha-(chloromercapto)-alpha-chloropropionate.

EXAMPLE 8

This example illustrates the preparation of ethyl alpha-(chloromercapto)-alpha-chloropropionate from ethyl alpha-(benzylmercapto)propionate and chlorine.

The procedure of Example 7 is followed except that the reaction is carried out under reflux and instead of charging to the system 50 parts by weight of sulfuryl chloride, chlorine gas is bubbled through the refluxing mass until approximately 26 parts by weight thereof is absorbed. Ethyl alpha-(chloromercapto)-alpha-chloropropionate is obtained.

In similar fashion other alpha-(chloromercapto)-alpha chloro-esters may be prepared from the corresponding alpha-(benzylmercapto) ester.

EXAMPLE 9

The procedure of Example 7 is followed except that in place of 22.4 parts by weight of ethyl alpha-(benzylmercapto)-propionate an equimolecular proportion of ethyl alpha-mercapto-propionate is charged to the reaction vessel. The use of ethyl alpha-mercapto-propionate simplifies the purification of the resultant ethyl alpha-(chloromercapto)-alpha-chloropropionate which is obtained as a product because the formation of liquid by-products is minimized by this procedure.

EXAMPLE 10

The procedure of Example 8 is followed except that in place of ethyl alpha-(benzylmercapto)-propionate an equimolecular proportion of ethyl alpha-mercapto-propionate is charged to the reaction vessel. As noted in Example 9 the purification of the resultant product ethyl alpha-(chloromercapto)-alpha-chloropropionate is simplified because the formation of liquid by-products is minimized by this procedure.

In similar fashion other alpha-(chloromercapto)-alpha-chloro esters may be prepared from the corresponding alpha-mercapto-esters and chlorine and/or sulfuryl chloride.

EXAMPLE 11

To a suitable reaction vessel equipped with a thermometer, agitator and venting means is charged approximately 23 parts by weight of alpha-mercapto-ortho-chloropropanilide dissolved in approximately 200 parts by weight of methylene chloride. While agitating the so-charged mass at about 0°C is slowly added approximately 43 parts by weight of sulfuryl chloride. The reaction is exothermic and the temperature during the addition is permitted to rise to about 20°C. Upon completion of the sulfuryl chloride addition, the mass is agitated for about two hours at about room temperature. Thereafter, the mass is stripped of volatiles under vacuum to give a solid residue which residue is dissolved in petroleum ether solvent, crystallized by cooling the solution to about −70°C., separated from the solvent by filtration and identified as alpha-chloro-alpha-(chloromercapto)-ortho-chloropropanilide.

Alpha-chloro-alpha-(chloromercapto)-ortho-chloropropanilide exhibits pre-emergent herbicidal activity against cocklebur and velvet leaf.

EXAMPLE 12

This example illustrates the preparation of alpha-chloro-alpha-(chloromercapto)-ortho-chloropropanilide from alpha-mercapto-ortho-chloropropanilide and chlorine.

The procedure of Example 11 is followed except that the reaction is carried out under reflux and instead of charging to the system 43 parts by weight of sulfuryl chloride, chlorine gas is bubbled through the refluxing mass until approximately 23 parts by weight thereof is absorbed. Alpha-chloro-alpha-(chloromercapto)-ortho-chloropropanilide is obtained.

In similar fashion other alpha-(chloromercapto)-alphachloro anilides may be prepared from the corresponding alphamercapto-anilides and chlorine and/or sulfuryl chloride.

EXAMPLE 13

The procedure of Example 11 is followed except that in place of alpha-mercapto-ortho-chloropropanilide and equimolecular proportion of N,N-di-ethyl-alpha-mercapto-propionamide is charged to the reaction vessel. N,N-di-ethyl-alpha-chloro-alpha-(chloro-mercapto)-propionamide is obtained.

EXAMPLE 14

The procedure of Example 12 is followed except that in place of alpha-mercapto-ortho-chloropropanilide an equimolecular proportion of N,N-di-ethyl-alpha-mercapto-propionamide is charged to the reaction vessel. N,N-di-ethyl-alpha-chloro-alpha-(chloromercapto)-propionamide is obtained.

In similar fashion other alpha-(chloromercapto)-alpha-chloro-amides may be prepared from the corresponding alpha-mercapto-amides and chlorine and/or sulfuryl chloride.

EXAMPLES 15 THROUGH 19

These examples illustrate the preparation of substituted alpha-chloro-methane-sulfenyl chlorides of the formula

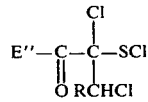

by the process of the present invention.

EXAMPLE 15

To a suitable reaction vessel equipped with a thermometer, agitator and venting means is charged approximately 25.6 parts by weight of alpha-(benzylmercapto)-propiophenone dissolved in approximately 300 parts by weight of 1,2-dichloroethane. While agitating the so-charged mass at about 0°C is slowly added approximately 30 parts by weight of sulfuryl chloride. The reaction is exothermic and the temperature during the addition is permitted to rise to about 20°C. Upon completion of the sulfuryl chloride addition, the mass is agitated for about three hours at about room temperature. Thereafter, the mass is stripped of volatiles under vacuum to give a liquid residue which residue is dissolved in petroleum ether solvent, crystallized by cooling the solution to about −70°C., separated from the solvent by filtration and identified as alpha-benzoyl-alphachloro-alpha-(chloromethyl)-methane sulfenyl chloride.

Alpha-benzoyl-alpha-chloro-alpha-(chloromethyl)-methane sulfenyl chloride was observed to be active as a pre-emergent herbicide to smartweed and velvet leaf.

EXAMPLES 16 THROUGH 18

The procedure of Example 15 is followed except that in place of alpha-(benzylmercapto)-propiophenone in the amount of about 25.6 parts by weight, a substituted alpha-(benzylmercapto)-propiophenone as shown in column A is added in an amount such that the molecular proportion of substituted alpha-(benzylmercapto)-propiophenone to sulfuryl chloride is 1 to 3. By this method, the corresponding substituted alpha-chloro-alpha-(chloromercapto)-propiophenone is prepared as shown in column B.

| EX. NO. | A | B |
|---------|---|---|
| 16 | alpha-(benzylmercapto)-para-chloropropiophenone | alpha-chloro-alpha-(para-chlorobenzoyl)-alpha-(chloromethyl)-methane-sulfenyl chloride |
| 17 | alpha-(benzylmercapto)-para-bromopropiophenone | alpha-chloro-alpha-(para-bromobenzoyl)-alpha-(chloromethyl)-methane-sulfenyl chloride |
| 18 | alpha-(benzylthio)-para-fluoropropiophenone | alpha-chloro-alpha-(para-fluorobenzoyl)-alpha-(chloromethyl)-methane-sulfenyl chloride |

EXAMPLE 19

The procedure of Example 15 is followed except that the reaction is carried out under reflux and, instead of charging to the system 30 parts by weight of sulfuryl chloride, chlorine gas is bubbled through the refluxing mass until approximately 16 parts by weight thereof is absorbed. Alpha-benzoyl-alpha-chloro-alpha-(chloromethyl)-methane-sulfenyl chloride is obtained. In this fashion, substituted alpha-chloro-alpha-benzoyl-alpha-(chloromethyl)methane-sulfenyl chlorides may likewise be prepared.

EXAMPLE 20

This example illustrates the preparation of intermediary products of the formula

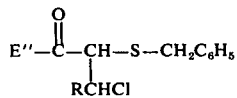

from the corresponding alpha-(benzylmercapto)-propiophenone and sulfuryl chloride.

To a suitable reaction vessel equipped with a thermometer, agitator and venting means is charged approximately 25.6 parts by weight of alpha-(benzylmercapto)-propiophenone dissolved in approximately 275 parts by weight of methylene chloride. While agitating the so-charged mass at about 0°C is slowly added approximately 13.4 parts by weight of sulfuryl chloride. The reaction is exothermic and the temperature during the addition is permitted to rise to about 20°C. Upon completion of the sulfuryl chloride addition, the mass is agitated for about one hour at about room temperature. Thereafter, the mass is stripped of volatiles under vacuum to give a liquid residue, which residue is dissolved in pentane, crystallized by cooling the solution to about −70°C., separated from the pentane by filtration and identified as alpha-(chloromethyl)-alpha-(benzylmercapto)-acetophenone.

In similar fashion, substituted alpha-(chloromethyl)-alpha-(benzylmercapto)-acetophenones can be prepared from the corresponding substituted alpha-(benzylmercapto)-propiophenones.

EXAMPLE 21

The procedure of Example 20 is followed except that the reaction is carried out under reflux and instead of charging to the system 13.4 parts by weight of sulfuryl chloride chlorine gas is bubbled through the refluxing mass until approximately 7 parts by weight thereof is absorbed. Alpha-(chloromethyl)-alpha-(benzylmercapto)-acetophenone is obtained.

In similar fashion, substituted alpha-(chloromethyl)-alpha-(benzylmercapto)-acetophenones can be prepared from the corresponding substituted alpha-(benzylmercapto)-propiophenones.

EXAMPLE 22

This example illustrates the preparation of intermediary products of the formula

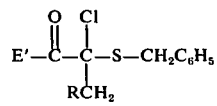

To a suitable reaction vessel equipped with a thermometer, agitator and venting means is charged approximately 22.4 parts by weight of ethyl alpha-(benzylmercapto)-propionate dissolved in approximately 275 parts by weight of methylene chloride. While agitating the so-charged mass at about 0°C is slowly added approximately 13.4 parts by weight of sulfuryl chloride. The reaction is exothermic and the temperature during the addition is permitted to rise to about 20°C. Upon completion of the sulfuryl chloride addition the mass is stripped of volatiles under vacuum to give a liquid residue which residue is purified by conventional means and is identified as ethyl alpha-(benzylmercapto)-alpha-chloropropionate.

EXAMPLE 23

This example illustrates the preparation of ethyl alpha-(benzylmercapto)-alpha-chloropropionate from ethyl alpha-(benzylmercapto)-propionate and chlorine.

The procedure of Example 22 is followed except that the reaction is carried out under reflux and instead of charging to the system 13.4 parts by weight of sulfuryl chloride, chlorine gas is bubbled through the refluxing mass until approximately 7.1 parts by weight thereof is absorbed. Ethyl alpha-(benzylmercapto)-alpha-chloropropionate is obtained.

In similar fashion other alpha-(benzylmercapto)-alpha chloro-esters may be prepared from the corresponding alpha-(benzylmercapto)-esters.

EXAMPLE 24

The procedure for testing pre-emergent herbicidal activity of representative substituted alpha-chloromethane-sulfenyl chlorides of this invention and their precursors and intermediaries is as follows:

A good grade of top soil is placed in aluminum pans and compacted to a depth of ⅜ to ½ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of application of 5 lbs. per acre. The pans are then placed on a sand bench in the greenhouse and watered from below as needed. The plants are observed at the end of approximately 14 days and the results recorded.

What is claimed is:

1. A compound having the formula

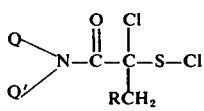

wherein
R is hydrogen or alkyl of 1 through 3 carbons, Q and Q' are independently selected from the group consisting of hydrogen, $C_{1-5}$ alkyl, lower alkoxyalkyl and the group

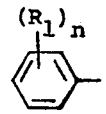

wherein
$R_1$ is selected from the group consisting of lower alkyl, halogen and $-CX_3$ where
X is halogen and n is an integer from 0—3 inclusive or Q and Q' may be combined to form an alkylene group having from 4 to 8 carbon atoms.

2. The compound of claim 1 wherein Q is phenyl and Q' is hydrogen.

3. The compound of claim 1 wherein Q is o-chlorophenyl and Q' is hydrogen.

* * * * *